United States Patent
Wu et al.

(10) Patent No.: US 10,005,068 B2
(45) Date of Patent: Jun. 26, 2018

(54) CATALYST AND MANUFACTURING METHOD THEREOF

(71) Applicant: INDUSTRIAL TECHNOLOGY RESEARCH INSTITUTE, Hsinchu (TW)

(72) Inventors: Kuo-Ching Wu, Kinmen County (TW); Chiou-Hwang Lee, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days. days.

(21) Appl. No.: 15/374,294

(22) Filed: Dec. 9, 2016

(65) Prior Publication Data

US 2017/0087536 A1    Mar. 30, 2017

Related U.S. Application Data

(62) Division of application No. 14/963,255, filed on Dec. 9, 2015, now Pat. No. 9,545,617.

(30) Foreign Application Priority Data

Dec. 9, 2014  (TW) .............................. 103142814 A
Jun. 5, 2015  (TW) .............................. 104118327 A

(51) Int. Cl.
  *B01J 21/02*  (2006.01)
  *B01J 21/04*  (2006.01)
  (Continued)

(52) U.S. Cl.
  CPC ............... *B01J 23/44* (2013.01); *B01J 21/10* (2013.01); *B01J 37/009* (2013.01); *B01J 37/035* (2013.01);
  (Continued)

(58) Field of Classification Search
  CPC ... B01J 21/02; B01J 21/04; B01J 21/10; B01J 23/007; B01J 23/02; B01J 23/40;
  (Continued)

(56) References Cited

U.S. PATENT DOCUMENTS 3,751,508 A * 8/1973 Fujiso .................... B01J 23/755
                                                            502/331
3,755,534 A * 8/1973 Graham ............... B01D 53/944
                                                            422/180

(Continued)

FOREIGN PATENT DOCUMENTS

CN          1766047 A      5/2006
CN        102093161 A      6/2011
(Continued)

OTHER PUBLICATIONS

Maegawa et al., "Efficient and Practical Arene Hydrogenation by Heterogeneous Catalysts under Mild Conditions", Chemistry—A European Journal, Jul. 2009, pp. 6953-6963.
(Continued)

*Primary Examiner* — Cam N. Nguyen
(74) *Attorney, Agent, or Firm* — Birch, Stewart, Kolasch & Birch, LLP

(57) ABSTRACT

A catalyst is provided. The catalyst includes a carrier and a metal. The carrier is represented by a formula: $M_xAl_{(1-x)}O_{(3-x)/2}$, where M is an alkaline earth metal, and x is between 0.09 and 0.24. The metal is loaded on the carrier. A method for manufacturing the catalyst is also provided.

17 Claims, 3 Drawing Sheets

(51) Int. Cl.
*B01J 21/10* (2006.01)
*B01J 23/00* (2006.01)
*B01J 23/02* (2006.01)
*B01J 23/40* (2006.01)
*B01J 23/44* (2006.01)
*B01J 23/56* (2006.01)
*B01J 23/58* (2006.01)
*B01J 37/00* (2006.01)
*B01J 37/03* (2006.01)
*B01J 37/04* (2006.01)
*B01J 37/06* (2006.01)
*B01J 37/08* (2006.01)
*C07C 41/20* (2006.01)
*C07C 67/303* (2006.01)

(52) U.S. Cl.
CPC ............... *B01J 37/06* (2013.01); *B01J 37/08* (2013.01); *C07C 41/20* (2013.01); *C07C 67/303* (2013.01)

(58) Field of Classification Search
CPC ... B01J 23/44; B01J 23/56; B01J 23/58; B01J 37/009; B01J 37/035; B01J 37/04; B01J 37/06; B01J 37/08
See application file for complete search history.

(56) References Cited

U.S. PATENT DOCUMENTS

| | | | |
|---|---|---|---|
| 4,001,343 A | 1/1977 | Gaillard et al. | |
| 4,110,258 A * | 8/1978 | Lauder | B01D 53/945 423/213.5 |
| 4,192,960 A | 3/1980 | Hillion et al. | |
| 4,261,862 A * | 4/1981 | Kinoshita | B01D 53/945 423/213.5 |
| 4,274,981 A * | 6/1981 | Suzuki | B01D 53/945 423/213.5 |
| 4,480,050 A * | 10/1984 | Brennan | B01J 23/58 423/213.5 |
| 4,503,273 A | 3/1985 | Mozdzen | |
| 4,522,792 A * | 6/1985 | Brennan | B01J 23/58 423/213.5 |
| 4,885,409 A | 12/1989 | Gardano et al. | |
| 5,204,309 A * | 4/1993 | Vorobley | B01D 53/864 502/306 |
| 5,942,645 A | 8/1999 | Rutter et al. | |
| 6,815,393 B2 * | 11/2004 | Noda | B01D 53/9422 502/243 |
| 6,858,193 B2 * | 2/2005 | Ruwisch | B01D 53/9422 423/213.5 |
| 7,361,319 B2 * | 4/2008 | Vierheilig | B01D 53/02 208/108 |
| 7,981,829 B2 * | 7/2011 | Wakabayashi | B01D 53/945 502/240 |
| 8,569,442 B2 | 10/2013 | Fung et al. | |
| 8,735,318 B2 * | 5/2014 | Nam | B01D 53/9422 423/239.1 |
| 9,561,494 B2 * | 2/2017 | Kato | F01N 3/103 |
| 2005/0085656 A1 | 4/2005 | Soloveichik et al. | |

FOREIGN PATENT DOCUMENTS

| | | |
|---|---|---|
| CN | 102211979 A | 10/2011 |
| CN | 102921440 A | 2/2013 |
| JP | 53-119854 A | 10/1978 |
| JP | 61-260034 A | 11/1986 |
| JP | 62-281832 A | 12/1987 |
| JP | 62-281833 A | 12/1987 |
| JP | 3-157342 A | 7/1991 |
| JP | 3-275637 A | 12/1991 |
| JP | 6-279339 A | 10/1994 |
| JP | 2000-63307 A | 2/2000 |
| JP | 2003-2853 A | 1/2003 |
| TW | 585850 B | 5/2004 |
| TW | 2010-08907 A | 3/2010 |
| WO | WO 2005/061106 A1 | 7/2005 |

OTHER PUBLICATIONS

Office Action of Taiwan Related Application, application No. 104118327, dated Dec. 23, 2015, p. 1-p. 9.
Terada, A., "The Isomers of the Hydrogenation Products of Bisphenol A. The Separations and Configurations of Three Isomers of 2,2-Bis-(4-hydroxycyclohexyl) propane and Two of 2-(4-Hydroxy-cyclohexyl)-2-(phydroxyphenyl) propane", Bull. of the Chem. Soc. of Japan 39(10), Oct. 1966, pp. 2194-2201.
Wang et al., "Catalytic hydrogenation of bisphenol A to hydrogenated bidphenol A", Speciality Petrochemicals, Sep. 2007, pp. 39-43.
Yen et al., "Hydrogenation of bisphenol A—Using a mesoporous silica based nano ruthenium catalyst Ru/MCM-41 and water as the solvent", Catalysis Today, Oct. 2, 2011, pp. 121-126.

* cited by examiner

CATALYST AND MANUFACTURING METHOD THEREOF

CROSS-REFERENCE TO RELATED APPLICATION

This is a divisional application of and claims the priority benefit of U.S. application Ser. No. 14/963,255, filed on Dec. 9, 2015, now allowed. The prior application Ser. No. 14/963,255 claims the priority benefit of Taiwan application serial no. 103142814, filed on Dec. 9, 2014, and Taiwan application serial no. 104118327, filed on Jun. 5, 2015. The entirety of each of the above-mentioned patent applications is hereby incorporated by reference herein and made a part of this specification.

TECHNICAL FIELD

The present disclosure relates to a catalyst and a method for manufacturing the same, and a method for manufacturing a hydrogenated bisphenol A or derivatives thereof using the catalyst.

BACKGROUND

Hydrogenated bisphenol A is the key raw material of certain unsaturated polyester resins and epoxy resins, and is capable of synthesizing specification materials having features of water resistance, agent resistance, thermal stability and light stability. Further, the materials synthesized by hydrogenated bisphenol A are currently applied to casting materials and coatings for outdoor electric appliance since the materials can also exhibit preferable weather resistance, corona resistance, tracking resistance, high dielectric strength and chemical reagent resistance.

However, because the existing industrial process for hydrogenated bisphenol A mostly adopts a batch high pressure process, problems including low catalyst productivity per unit, low catalyst selectivity and poor catalyst stability are still bottlenecks to overcome. Accordingly, it is an issue that needs to be solved as how to improve hydrogenation activity for reducing reaction pressure, increase catalyst selectivity for reducing generation of byproducts, and extend catalyst lifetime for reducing costs.

SUMMARY

The present disclosure provides a catalyst, which includes a carrier and a metal. The carrier is represented by a formula: $M_xAl_{(1-x)}O_{(3-x)/2}$, where M is an alkaline earth metal, and x is between 0.09 and 0.24. The metal is loaded on the carrier.

The present disclosure also provides a method for manufacturing a catalyst, which includes preparing a carrier and loading a metal on the carrier.

To make the above features and advantages of the present disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION

Figure 1:
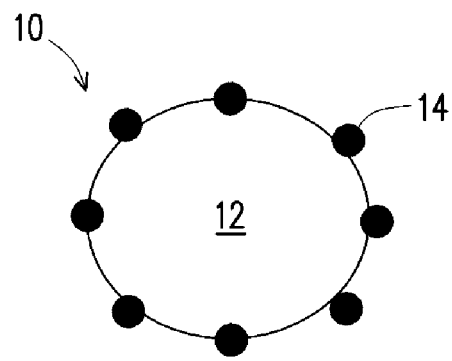
FIG. 1 is a schematic structural diagram of a catalyst according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
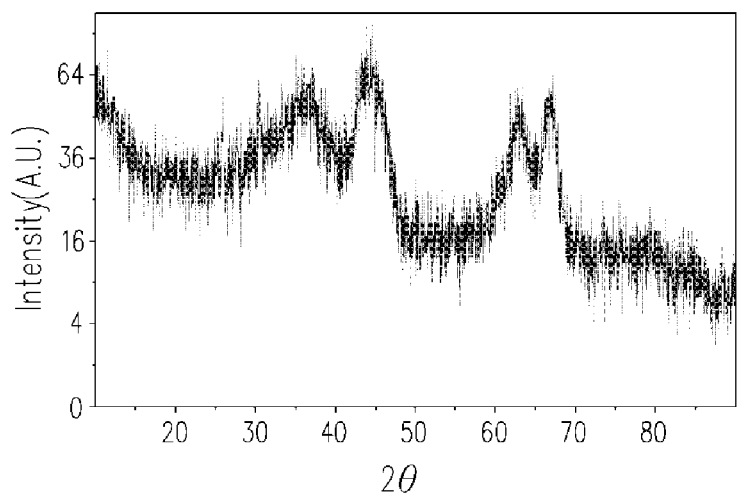
FIG. 2 is an X-ray diffraction (XRD) diagram of a carrier according to an embodiment of the present disclosure.

FIG. 1 is a schematic structural diagram of a catalyst according to an embodiment of the present disclosure. FIG. 2 is an X-ray diffraction (XRD) diagram of a carrier according to an embodiment of the present disclosure.

Referring to FIG. 1, a catalyst 10 includes a carrier 12 and a Pd metal 14. The carrier 12 may be represented by a formula: $M_xAl_{(1-x)}O_{(3-x)/2}$. M is an alkaline earth metal, and x is between 0.09 and 0.24. The alkaline earth metal is, for example, Mg, Ca or a combination thereof, but the present disclosure is not limited thereto. Further, referring to FIG. 2, in one embodiment, the carrier 12 is in an amorphous phase. The Pd metal 14 is loaded on the carrier 12. In one embodiment, based on the carrier 12, the Pd metal 14 is contained in an amount of between 0.5 wt % and 3 wt %.

According to embodiments of the present disclosure, the carrier 12 includes the alkaline earth metal and Al to load the Pd metal, and is capable of improving a hydrogenation ability to reduce a reaction pressure for the hydrogenation. Furthermore, the alkaline earth metal is bonded to Al of the carrier 12 to prevent catalyst loss, so that a life time of the catalyst is extended. In addition, the alkaline earth metal and Al are uniformly distributed to reduce strong acid points on a surface of the catalyst, so as to reduce cracking and dehydroxylated byproducts and increase catalyst selectivity.

Figure 3:
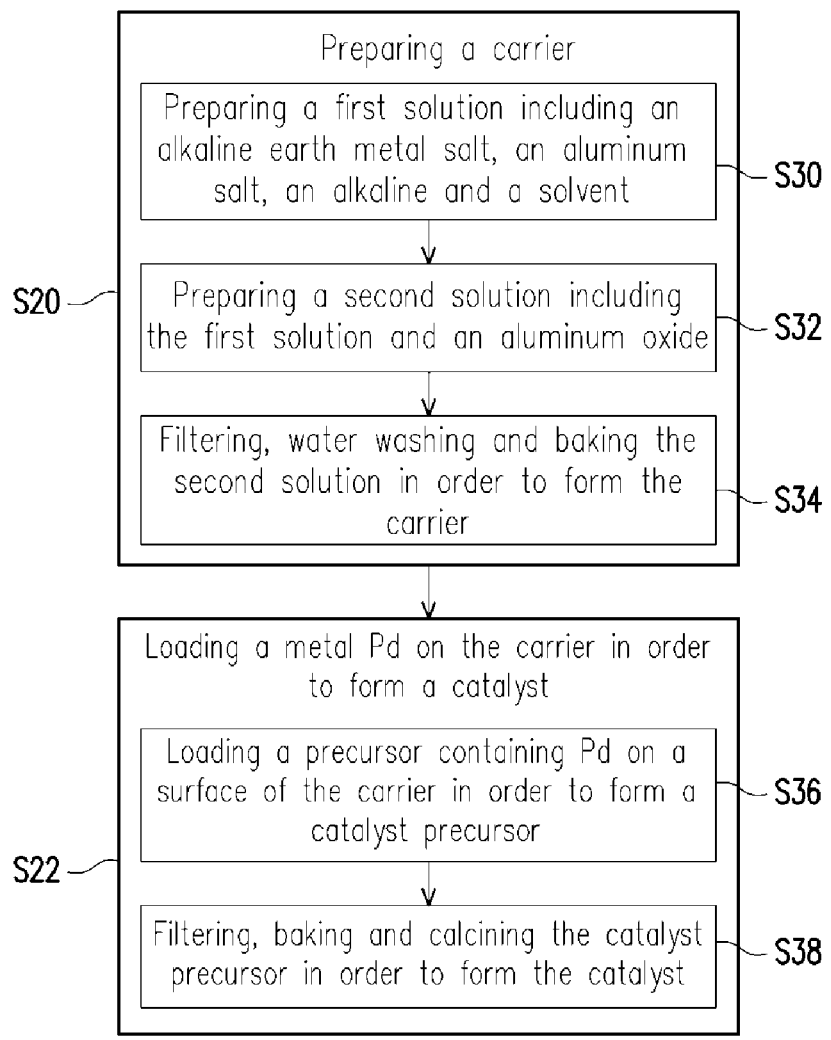
FIG. 3 is a schematic diagram of a manufacturing process of a catalyst according to an embodiment of the present disclosure.

FIG. 3 is a schematic diagram of a manufacturing process of a catalyst according to an embodiment of the present disclosure.

Referring to FIG. 3, a method for manufacturing a catalyst includes: after a carrier is prepared in step S20, a Pd metal is loaded on the carrier in step S22.

Step S20 for preparing the carrier may include step S30, step S32 and step S34. Specifically, in step S30, a first solution is prepared. The first solution includes an alkaline earth metal salt, an aluminum salt, an alkaline and a solvent. In one specific embodiment, the first solution may be formed by mixing and stirring an alkaline solution with the solvent in which the alkaline earth metal salt and the aluminum salt are dissolved. The alkaline earth metal salt may be, for example, an alkaline earth metal nitrate, an alkaline earth metal sulfate, an alkaline earth metal carbonate, or an alkaline earth metal chloride. In an exemplary embodiment, the alkaline earth metal salt is, for example, magnesium nitrate, magnesium sulfate, magnesium carbonate, magnesium chloride, calcium nitrate, calcium sulfate or calcium chloride. The aluminum salt is, for example, aluminum nitrate, aluminum sulfate, aluminum carbonate, aluminum oxide, aluminum hydroxide, or aluminum chloride. In one embodiment, a mole ratio of the alkaline earth metal and Al is, for example, (0.5 to 1.5):1. The solvent is, for example, a deionized water or a monohydric alcohol. In one exemplary embodiment, the alkaline solution is, for example, a deionized water solution containing sodium hydroxide, sodium carbonate or a combination thereof. The pH value of the alkaline solution is, for example, between 8 and 12. In one embodiment, a temperature used for mixing and stirring is, for example, at 25° C. (room temperature) to 100° C. In one embodiment, a time used for mixing and stirring is, for example, 4 to 18 hours.

Next, in step S32, a second solution is prepared. The second solution includes the first solution and an aluminum oxide. More specifically, the second solution is formed by adding the aluminum oxide into the first solution followed by continuously mixing and stirring. In one embodiment, a mole ratio of Al in the aluminum oxide and the alkaline earth metal is, for example, (1 to 5):1. In one embodiment, a temperature used for mixing and stirring is, for example, at 25° C. (room temperature) to 60° C. In one embodiment, a time used for mixing and stirring is, for example, 1 to 18 hours.

Subsequently, in step S34, the second solution subjected to coprecipitating, filtering, water washing and baking so as to form the carrier 12. The carrier 12 may be represented by a formula: $M_xAl_{(1-x)}O_{(3-x)/2}$, where M is an alkaline earth metal, and x is between 0.09 and 0.24. In one embodiment, the baking is performed at 100° C. to 130° C. for 4 to 18 hours. Sieving may be performed first before baking. In one embodiment, a carrier size after sieving is, for example, 100 mesh or less. In another embodiment, shaping and sieving may be performed on the carrier first, and the carrier size after screening is, 20 to 30 mesh.

Then, in step S22, the Pd metal is loaded on the carrier. Step S22 may include step S36 and step S38. More specifically, in step S36, a precursor containing Pd is loaded on a surface of the carrier 12 in order to form a catalyst precursor. The precursor containing Pd includes, for example, palladium chloride ($PdCl_2$), palladium nitrate ($Pd(NO_3)_2$) or palladium acetate ($Pd(CH_3COO)_2$). In one embodiment, the precursor containing Pd is loaded on the surface of the carrier 12 by using, for example, incipient wetness impregnation or deposition-precipitation. In one exemplary embodiment, the incipient wetness impregnation is used to prepare an impregnation solution by adding the palladium chloride into a proper amount of the deionized water. The incipient wetness impregnation is performed at 25° C. (room temperature) to 60° C. for 1 hour to 4 hours, for example. In the prepared impregnation solution, a concentration range of Pd is 1 wt % to 5 wt %, for example.

Next, in step S38, the catalyst precursor is subjected to filtering, baking and calcining, so as to form a Pd metal 14 loaded catalyst 10. In one exemplary embodiment, the baking is performed at 100° C. to 130° C. for 4 to 18 hours. The calcining is performed at 300° C. to 550° C. for 4 to 18 hours, for example. In one embodiment, in the Pd metal 14 loaded catalyst 10, the Pd metal 14 is contained in an amount of between 0.5 wt % and 3 wt % based on the carrier 12.

Figure 4:
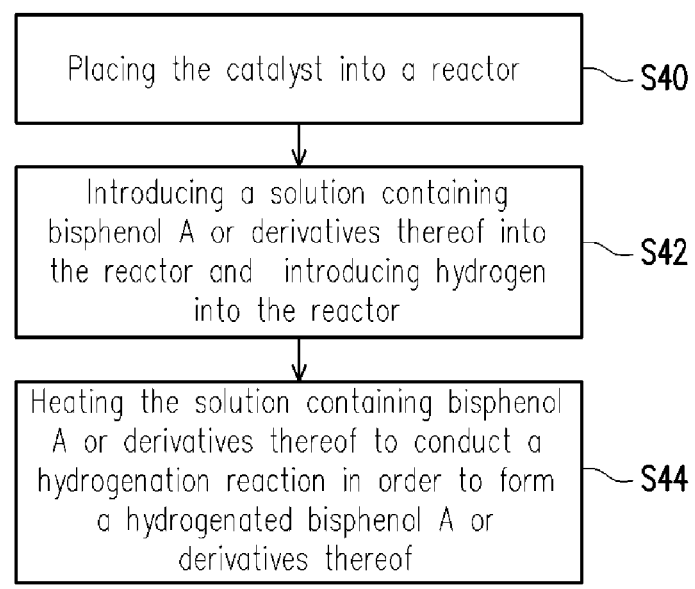
FIG. 4 is a schematic diagram of a manufacturing process of a hydrogenated bisphenol A or derivatives thereof according to an embodiment of the present disclosure.

FIG. 4 is a schematic diagram of a manufacturing process of a hydrogenated bisphenol A or derivatives thereof according to an embodiment of the present disclosure.

Referring to FIG. 1 and FIG. 4, first, in step S40, the catalyst 10 is placed into a reactor. The catalyst 10 includes the carrier 12 and the Pd metal 14. The carrier 12 may be represented by a formula: $M_xAl_{(1-x)}O_{(3-x)/2}$, where M is an alkaline earth metal, and x is between 0.09 and 0.24. The alkaline earth metal includes Mg or Ca, but the present disclosure is not limited thereto. In one embodiment, the carrier 12 is in an amorphous phase. The Pd metal 14 is loaded on the carrier 12. In one embodiment, the Pd metal 14 is contained in an amount of between 0.5 wt % and 3 wt % based on the carrier 12. In one embodiment, the reactor is, for example, a fixed bed or a trickle bed.

Next, in step S42, a solution containing bisphenol A or derivatives thereof is introduced into the reactor and hydrogen is introduced into the reactor. The solution containing bisphenol A or derivatives thereof includes bisphenol A or derivatives thereof and a solvent. In one embodiment, the solvent is, for example, a monohydric alcohol. In one exemplary embodiment, the solvent includes, for example, methanol, ethanol, propanol, isopropanol, cyclohexanol, nonanol, or a combination thereof. Bisphenol A or derivatives thereof may be transported into the reactor continuously by using, for example, a pump. In one embodiment, a feed concentration of bisphenol A or derivatives thereof is, for example, 5 wt % to 30 wt %. In another embodiment, the feed concentration of bisphenol A or derivatives thereof is, for example, 10 wt % to 25 wt %. In one embodiment, bisphenol A derivatives include

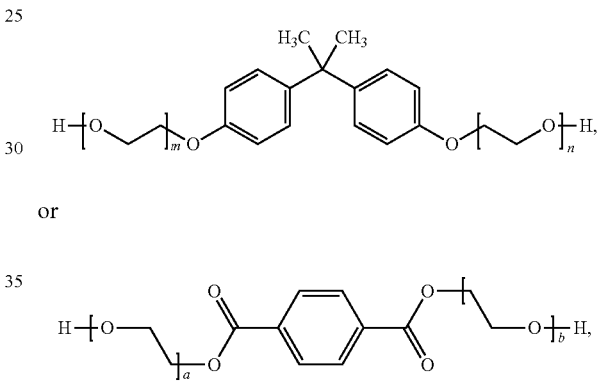

or where a, b=1-2.

In one embodiment, a feed rate (liquid hourly space velocity; LHSV) of the solution containing bisphenol A or derivatives thereof is, for example, 1/h to 6/h. In another embodiment, the feed rate (LHSV) of the solution containing bisphenol A or derivatives thereof is, for example, 1/h to 3/h. Hydrogen and the solution containing bisphenol A or derivatives thereof may be introduced into the reactor at the same time, or a precedence of the two may be adjusted according to practical demands. In the reactor, a mole ratio of hydrogen/bisphenol A or derivatives thereof is, for example, 6 to 30. In another embodiment, the mole ratio of hydrogen/bisphenol A or derivatives thereof is, for example, 6 to 20.

Lastly, in step S44, the solution containing bisphenol A or derivatives thereof is heated to conduct a hydrogenation reaction in order to form a product containing a hydrogenated bisphenol A or derivatives thereof. In one embodiment, a temperature used for heating the solution containing bisphenol A or derivatives thereof is heated at, 100° C. to 200° C., for example. In another embodiment, the temperature used for heating the solution containing bisphenol A or derivatives thereof is, for example, at 120° C. to 180° C. The reaction pressure is less than or equal to 70 bar. In one embodiment, the reaction pressure is, for example, 5 bar to 70 bar. In another embodiment, the reaction pressure is, for example, 10 bar to 50 bar. In other embodiments, the reaction pressure is, for example, less than or equal to 30 bar.

The hydrogenated bisphenol A or derivatives thereof may be obtained after removing the solvent from the product containing the hydrogenated bisphenol A or derivatives thereof. The solvent may be recycled and reused through distillation.

In the hydrogenation of bisphenol A or derivatives thereof conducted by adopting the catalyst of the present disclosure, an experimental result shows that when the reaction pressure is 70 bar or less, a catalyst productivity per unit of the hydrogenated bisphenol A or derivatives thereof can reach 1000 g/g catalyst or more, and a purity of the hydrogenated bisphenol A or derivatives thereof can reach 97% or more. In addition, during the hydrogenation reaction conducted by adopting the catalyst of the present disclosure, the catalyst can still maintain stable performance even after continuous reaction for 2500 hours without additional adding water to serve as a stabilizer.

Various methods for preparing the catalyst are provided as examples below, but the present disclosure is not limited thereto.

Preparing a catalyst A (carrier: $M_xAl_{(1-x)}O_{(3-x)/2}$, x:0.2):

First, 1 liter deionized water solution containing 256 g magnesium nitrate and 357 g aluminum nitrate is added into a deionized water solution containing sodium hydroxide or sodium carbonate (or a mixture the two) followed by agitating for 4 hours at room temperature to 100° C. Next, 145 g aluminum oxide powder is further added followed by continuously mixing and stirring. Next, a filter cake is obtained after filtering. The obtained filter cake is water washed and baked. The baked filter cake is crashed to 100 mesh or less and shaped into particles of 20 to 30 mesh to forma carrier of a catalyst A. 30 g of the carrier is added to the solution containing 0.25 g $PdCl_2$ to perform incipient wetness impregnation. The impregnation solution is prepared by using $PdCl_2$ as the precursor followed by adding a proper amount of the deionized water thereto so that the impregnation solution contains a desirable metal concentration. The impregnated catalyst is filtered and baked, and then calcined for 4 hours at 450° C. in order to form a catalyst with a carrier ($M_xAl_{(1-x)}O_{(3-x)/2}$, x:0.2).

Preparing a catalyst B (carrier: $M_xAl_{(1-x)}O_{(3-x)/2}$, x:0.09):

Other than the additive amount of the aluminum oxide powder being changed to 360 g, the preparing method herein is identical to that of the catalyst A. The impregnated catalyst is filtered and baked, and calcined for 4 hours at 450° C. in order to form a catalyst of a carrier ($M_xAl_{(1-x)}O_{(3-x)/2}$, x:0.09).

Preparing a catalyst C (carrier: $M_xAl_{(1-x)}O_{(3-x)/2}$, x:0.15):

Other than the additive amount of the aluminum oxide powder being changed to 200 g, the preparing method herein is identical to that of the catalyst A. The impregnated catalyst is filtered and baked, and calcined for 4 hours at 450° C. in order to form a catalyst with a carrier ($M_xAl_{(1-x)}O_{(3-x)/2}$, x:0.15).

Preparing a catalyst D (carrier: $M_xAl_{(1-x)}O_{(3-x)/2}$, x:0.10):

Other than the additive amount of the aluminum oxide powder being changed to 320 g, the preparing method herein is identical to that of the catalyst A. The impregnated catalyst is filtered and baked, and calcined for 4 hours at 450° C. in order to form a catalyst with a carrier ($M_xAl_{(1-x)}O_{(3-x)/2}$, x:0.10).

EXPERIMENTAL EXAMPLES

Various experimental examples are provided below and served to further describe application of the catalyst A to the catalyst D used in the hydrogenation reaction of bisphenol A or derivatives thereof for manufacturing the hydrogenated bisphenol A or derivatives thereof.

Example 1 to Example 3

First, 3 ml catalyst A (containing 1 wt % Pd) of 20 to 30 mesh is placed into a fixed-bed reactor, and a hydrogenation experiment is performed on a 15 wt % bisphenol A (BPA) isopropanol solution by using a continuous-type trickle-bed mode. Reaction conditions include: a 15 wt % BPA solution, a liquid flow rate at 6 ml/h, a reaction temperature at 160° C., and a hydrogen flow rate at 65 ml/min. Besides, the reaction pressures of Example 1, Example 2 and Example 3 are respectively 10 bar, 20 bar and 30 bar. The analyzed results obtained by gas chromatography (GC) analyzer are shown by Table 1 below.

TABLE 1

|  | Example 1 | Example 2 | Example 3 |
| --- | --- | --- | --- |
| Reaction pressure, bar | 10 | 20 | 30 |
| Bisphenol A conversion rate, % | 99.2 | 99.6 | 99.8 |
| Hydrogenated bisphenol A selectivity, % | 98.2 | 98.9 | 99.4 |
| Pyrolysis byproduct selectivity, % | 0.8 | 0.2 | 0.1 |
| Dehydroxylated byproduct, % | 0.6 | 0.4 | 0.2 |

In view of Table 1, it can be known that in Example 1 to Example 3, when the reaction pressure is between 10 bar and 30 bar, the conversion rate of the bisphenol A can reach 99.2% or more; the selectivity of the hydrogenated bisphenol A can reach 98.2% or more; the selectivity of the pyrolysis byproduct is 0.8% or less; and the dehydroxylated byproducts are 0.6% or less. Therefore, the catalyst manufactured according to the present disclosure can provide favorable efficiency in the hydrogenation reaction of bisphenol A or derivatives thereof when the reaction pressures are less than 70 bar.

Example 4 to Example 6

First, 3 ml catalyst A (containing 1 wt % Pd) of 20 to 30 mesh is placed into a fixed-bed reactor, and a hydrogenation experiment is performed on a bisphenol A (BPA) isopropanol solution by using the continuous-type trickle-bed mode. Reaction conditions include: bisphenol A (BPA) isopropanol solutions (10 wt %, 15 wt % and 20 wt % in Example 4, Example 5 and Example 6 respectively), a liquid flow rate at 6 ml/h, a reaction temperature at 160° C., a reaction pressure at 30 bar, and a hydrogen flow rate at 65 ml/min. The analyzed results obtained by gas chromatography analyzer are shown by Table 2 below.

TABLE 2

|  | Example 4 | Example 5 | Example 6 |
| --- | --- | --- | --- |
| Bisphenol A concentration, % | 10 | 15 | 20 |
| Bisphenol A conversion rate, % selectivity, % | 99.8 | 99.8 | 99.8 |
| Hydrogenated bisphenol A | 99.0 | 99.4 | 99.4 |
| Pyrolysis byproduct selectivity, % | 0.1 | 0.1 | 0.1 |
| Dehydroxylated byproduct, % | 0.2 | 0.2 | 0.2 |

In view of Table 2, it can be known that in Example 4 to Example 6, when the concentration of the bisphenol A is between 10 wt % and 20 wt %, the conversion rate of the bisphenol A can reach 99.8%; the selectivity of the hydrogenated bisphenol A can reach 99.0% or more; the selectivity of the pyrolysis byproduct is 0.1% or less; and the dehydroxylated byproducts are 0.2% or less. Therefore, the catalyst manufactured according to the present disclosure can provide favorable efficiency in the hydrogenation reaction of bisphenol A when the concentration of the bisphenol A is between 10 wt % and 20 wt %.

Example 7

First, 3 ml catalyst B (containing 1 wt % Pd) of 20 to 30 mesh is placed into a fixed-bed reactor, and a hydrogenation experiment is performed by the continuous-type trickle-bed mode. The solvent is changed to the cyclohexanol in the hydrogenation experiment of Example 7. Reaction conditions include: a 10 wt % BPA solution, a solvent being cyclohexanol, a liquid flow rate at 6 ml/h, a reaction temperature at 160° C., a reaction pressure at 30 bar, and a hydrogen flow rate at 65 ml/min. The analyzed results obtained by gas chromatography analyzer are shown by Table 3 below.

TABLE 3

|  | Example 7 |
|---|---|
| Solvent | Cyclohexanol |
| Bisphenol A conversion rate, % | 100 |
| Hydrogenated bisphenol A selectivity, % | 98.4 |
| Pyrolysis byproduct selectivity, % | 0.2 |
| Dehydroxylated byproduct, % | 1.6 |

In view of Table 3, it can be known that when the solvent is changed to the cyclohexanol, the conversion rate of the bisphenol A conversion rate can reach 100% despite the dehydroxylated byproduct (1.6%) is greater than the conversion rate of that using the solvent being isopropanol (the dehydroxylated byproduct thereof is 0.2%). Therefore, the catalyst manufactured according to the present disclosure can provide favorable efficiency in the hydrogenation reaction of bisphenol A so long as the monohydric alcohol is used as the solvent.

Example 8 to Example 10

First, 3 ml catalyst C (containing 1 wt % Pd) of 20 to 30 mesh is placed into a fixed-bed reactor, and a hydrogenation experiment is performed on a bisphenol A (BPA) isopropanol solution by using the continuous-type trickle-bed mode. Reaction conditions include: a 15 wt % BPA isopropanol solution, a liquid flow rate at 6 ml/h, a reaction pressure at 30 bar, and a hydrogen flow rate at 65 ml/min. Besides, the reaction temperatures of Example 8, Example 9 and Example 10 are at 140° C., 160° C. and 180° C. respectively. The analyzed results obtained by gas chromatography analyzer are shown by Table 4 below.

TABLE 4

|  | Example 8 | Example 9 | Example 10 |
|---|---|---|---|
| Reaction temperature, ° C. | 140 | 160 | 180 |
| Bisphenol A conversion rate, % | 99.7 | 99.8 | 100 |
| Hydrogenated bisphenol A selectivity, % | 99.6 | 99.4 | 99.3 |

TABLE 4-continued

|  | Example 8 | Example 9 | Example 10 |
|---|---|---|---|
| Pyrolysis byproduct selectivity, % | 0.1 | 0.1 | 0.3 |
| Dehydroxylated byproduct, % | 0.1 | 0.2 | 0.2 |

In view of Table 4, it can be known that in Example 8 to Example 10, when the reaction temperature is at 140° C. to 180° C., the conversion rate of the bisphenol A can reach 99.7% or more; the selectivity of the hydrogenated bisphenol A can reach 99.3% or more; the selectivity of the pyrolysis byproduct is 0.3% or less; and the dehydroxylated byproducts are 0.2% or less. Therefore, the catalyst manufactured according to the present disclosure can provide favorable efficiency in the hydrogenation reaction of bisphenol A when the reaction temperature is between 140° C. and 180° C.

Example 11 to Example 13

First, 6 ml catalyst C (containing 1 wt % Pd) of 20 to 30 mesh is placed into a fixed-bed reactor, and then a continuous-type trickle-bed mode is used to perform a hydrogenation experiment. Reaction conditions include: a 15 wt % BPA solution, a solvent being isopropanol a reaction temperature at 160° C., a reaction pressure at 30 bar, and a hydrogen flow rate at 65 ml/min. Besides, the liquid flow rates of Example 11, Example 12 and Example 13 are 6 ml/h, 12 ml/h and 18 ml/h respectively. The analyzed results obtained by gas chromatography analyzer are shown by Table 5 below.

TABLE 5

|  | Example 11 | Example 12 | Example 13 |
|---|---|---|---|
| Feed rate, ml/h | 6 | 12 | 18 |
| Bisphenol A conversion rate, % | 100 | 100 | 99.6 |
| Hydrogenated bisphenol A selectivity, % | 99.2 | 99.4 | 99.5 |
| Pyrolysis byproduct selectivity, % | 0.2 | 0.1 | 0.1 |
| Dehydroxylated byproduct, % | 0.2 | 0.2 | 0.1 |

In view of Table 5, it can be known that in Example 11 to Example 13, when the feed rates of bisphenol A are between 6 ml/h and 18 ml/h, the conversion rates of the bisphenol A can reach 99.6% or more; the selectivity of the hydrogenated bisphenol A can reach 99.2% or more; the selectivity of the pyrolysis byproduct is 0.2% or less; and the dehydroxylated byproducts are 0.2% or less. Therefore, the catalyst manufactured according to the present disclosure can still provide favorable efficiency in the hydrogenation reaction of bisphenol A when the feed rate of bisphenol A is between 6 ml/h and 18 ml/h.

Example 14 to Example 19

First, 12 ml (approximately 8 g) catalyst C (containing 1 wt % Pd) of 20 to 30 mesh is placed into a fixed-bed reactor, and a hydrogenation experiment is performed on a bisphenol A (BPA) isopropanol solution by using the continuous-type trickle-bed mode. Reaction conditions include: a 15 wt % to 20 wt % BPA isopropanol solution, a liquid flow rate between 24 ml/h to 27 ml/h, a reaction temperature at 155° C. to 160° C., a reaction pressure at 30 bar, and a hydrogen flow rate at 65 ml/min. The analyzed results obtained by gas chromatography analyzer are as shown by Table 6 below.

TABLE 6

| | Example 14 | Example 15 | Example 16 | Example 17 | Example 18 | Example 19 |
|---|---|---|---|---|---|---|
| Reaction Time, hours | 24 | 500 | 1000 | 1560 | 2000 | 2500 |
| Bisphenol A conversion rate, % | 100 | 100 | 100 | 100 | 100 | 100 |
| Hydrogenated bisphenol A selectivity, % | 99.4 | 99.3 | 99.5 | 99.5 | 99.4 | 99.3 |
| Pyrolysis byproduct selectivity, % | 0.1 | 0.1 | 0.1 | 0.1 | 0.1 | 0.1 |
| Dehydroxylated byproduct, % | 0.1 | 0.1 | 0.1 | 0.1 | 0.2 | 0.2 |

In view of Table 6, it can be known that in Example 14 to Example 19, the conversion rates of the bisphenol A can reach 100%; the selectivity of the hydrogenated bisphenol A can reach 99.3% or more; the selectivity of the pyrolysis byproduct are 0.1% or less; and the dehydroxylated byproduct are 0.2% or less. Accordingly, the experimental result shows that with use of the catalyst manufactured according to the present disclosure in the hydrogenation reaction of bisphenol A, the catalyst can still maintain stable performance even after continuous reaction for 2500 hours without additional adding water to serve as a stabilizer during the reaction process.

Example 20 to Example 23

First, 3 ml catalysts A to D of 20 to 30 mesh are placed into a fixed-bed reactor, respectively. A hydrogenation experiment is performed on a 15 wt % bisphenol A (BPA) isopropanol solution by using the continuous-type trickle-bed mode. Reaction conditions include: 15 wt % BPA solution, a liquid flow rate at 6 ml/h, reaction temperature at 160° C., reaction pressure at 30 bar, and a hydrogen flow rate at 65 ml/min. The analyzed results obtained by gas chromatography analyzer are shown by Table 7 below.

TABLE 7

| | Example 20 | Example 21 | Example 22 | Example 23 |
|---|---|---|---|---|
| Catalyst | B | D | C | A |
| $M_xAl_{(1-x)}O_{(3-x)/2}$, where x = | 0.09 | 0.10 | 0.15 | 0.20 |
| Bisphenol A conversion rate, % | 100 | 100 | 99.8 | 99.8 |
| Hydrogenated bisphenol A selectivity, % | 98.2 | 98.7 | 99.4 | 99.4 |
| Pyrolysis byproduct selectivity, % | 0.8 | 0.5 | 0.1 | 0.1 |
| Dehydroxylated byproduct, % | 0.7 | 0.4 | 0.2 | 0.2 |

In view of Table 7, it can be known that in Example 20 to Example 23, when the catalysts A to D manufactured according to the present disclosure are used, the conversion rates of the bisphenol A can reach 99.8% or more; the selectivity of the hydrogenated bisphenol A can reach 98.2% or more; the selectivity of the pyrolysis byproduct are 0.8% or less; and the dehydroxylated byproducts are 0.7% or less. Therefore, in the hydrogenation reaction of bisphenol A, all of the catalysts with different component ratios (based on the carrier, a percentage by weight of magnesium oxide accounts for 7 to 16 wt %) can provide favorable efficiency.

Example 24 to Example 25

First, 12 ml (approximately 8 g) catalyst C (containing 2 wt % Pd) of 20 to 30 mesh is placed into a fixed-bed reactor, and a hydrogenation experiment is performed on bisphenol A derivative (ethoxylated bisphenol A (BPA2), and a structure thereof is shown by the following formula, where m, n=1) isopropanol solution by using the continuous-type trickle-bed mode.

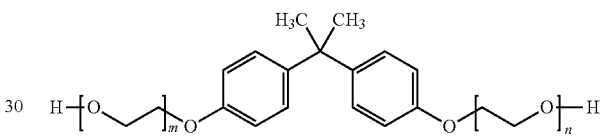

Reaction conditions include: a 15 wt % BPA2 isopropanol solution, a liquid flow rate between 6 ml/h to 12 ml/h, a reaction temperature at 170° C., a reaction pressure at 40 bar, and a hydrogen flow rate at 65 ml/min. The analyzed results obtained by gas chromatography analyzer are as shown by Table 8 below.

TABLE 8

| | Example 24 | Example 25 |
|---|---|---|
| Feed rate, ml/h | 12 | 6 |
| BPA2 conversion rate, % | 98 | 99 |
| Hydrogenated BPA2 selectivity, % | 97 | 99 |
| Pyrolysis byproduct selectivity, % | 0.1 | 0.1 |
| Dehydroxylated byproduct, % | 0.1 | 0.1 |

In view of Table 8, it can be known that in Example 24 to Example 25, when different feed rates and the same temperature 170° C. are used, the conversion rate of the bisphenol A derivative can reach 98% or more; the selectivity of the hydrogenated bisphenol A derivative can reach 97% or more; the selectivity of the pyrolysis byproduct is 0.1% or less; and the dehydroxylated byproducts are 0.1% or less. Therefore, the catalyst manufactured according to the present disclosure can provide favorable efficiency in the hydrogenation reaction of bisphenol A derivative when the reaction pressures are less than 70 bar.

Example 26

First, 12 ml (approximately 8 g) catalyst C (containing 2 wt % Pd) of 20 to 30 mesh is placed into a fixed-bed reactor, and a hydrogenation experiment is performed on bisphenol A derivative (ethoxylated bisphenol A (BPA4), and a structure thereof is shown by the following formula, where m, n=2) isopropanol solution by using the continuous-type trickle-bed mode.

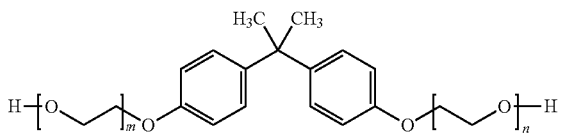

Reaction conditions include: a 15 wt % BPA4 isopropanol solution, a liquid flow rate between 6 ml/h, a reaction temperature at 170° C., a reaction pressure at 40 bar, and a hydrogen flow rate at 65 ml/min. The analyzed results obtained by gas chromatography analyzer are as shown by Table 9 below.

TABLE 9

|  | Example 26 |
| --- | --- |
| Feed rate, ml/h | 6 |
| BPA4 conversion rate, % | 99 |
| Hydrogenated BPA4 selectivity, % | 99 |
| Pyrolysis byproduct selectivity, % | 0.1 |
| Dehydroxylated byproduct, % | 0.1 |

In view of Table 9, it can be known that in Example 26, the conversion rate of the bisphenol A derivative BPA4 can reach 99% or more; the selectivity of the hydrogenated bisphenol A derivative can reach 99% or more; the selectivity of the pyrolysis byproduct is 0.1% or less; and the dehydroxylated byproducts are 0.1% or less. Therefore, the catalyst manufactured according to the present disclosure can still provide favorable efficiency in the hydrogenation reaction of bisphenol A derivative BPA4 when the feed rate of bisphenol A is between 6 ml/h and 18 ml/h.

Example 27

First, 12 ml (approximately 8 g) catalyst C (containing 2 wt % Pd) of 20 to 30 mesh is placed into a fixed-bed reactor, and a hydrogenation experiment is performed on ethoxylated tert-phthalicacid (TPA2, and a structure thereof is shown by the following formula, where a, b=1) isopropanol solution by using the continuous-type trickle-bed mode.

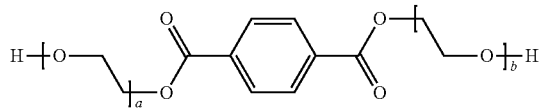

Reaction conditions include: a 15 wt % TPA2 isopropanol solution, a liquid flow rate between 6 ml/h, a reaction temperature at 170° C., a reaction pressure at 40 bar, and a hydrogen flow rate at 65 ml/min. The analyzed results obtained by gas chromatography analyzer are as shown by Table 10 below.

TABLE 10

|  | Example 27 |
| --- | --- |
| Feed rate, ml/h | 6 |
| TPA2 conversion rate, % | 99.1 |

TABLE 10-continued

|  | Example 27 |
| --- | --- |
| Hydrogenated TPA2 selectivity, % | 99.2 |
| Pyrolysis byproduct selectivity, % | 0.2 |
| Dehydroxylated byproduct, % | 0.1 |

In view of Table 10, it can be known that in Example 27, the conversion rate of the bisphenol A derivative TPA2 can reach 99% or more; the selectivity of the hydrogenated bisphenol A derivative can reach 99% or more; the selectivity of the pyrolysis byproduct is 0.2%; and the dehydroxylated byproducts is 0.1% or less. Therefore, the catalyst manufactured according to the present disclosure can still provide favorable efficiency in the hydrogenation reaction of bisphenol A derivative TPA2 when the feed rate of bisphenol A is 6 ml/h.

In the catalyst of the present disclosure, because the aluminum-magnesium mixed oxide (i.e., the carrier) is in amorphous phase and there is the bond formed between the alkaline earth metal and Al, the catalyst loss may be prevented in order to extend the lifetime of the catalyst. In addition, the alkaline earth metal and Al are uniformly distributed to reduce the strong acid points on the surface of the catalyst, so that the cracking and dehydroxylated byproducts may be reduced and the catalyst selectivity may be increased.

In summary, in the catalyst of the present disclosure, since the carrier directly formed by the alkaline earth metal and Al is configured to load the Pd metal, the hydrogenation activity and the catalyst productivity may be effectively improved to reduce the pressure during the hydrogenation reaction (to 30 bar or less). Further, in the catalyst of the present disclosure, because the bond formed between the alkaline earth metal and Al may prevent the catalyst loss during the hydrogenation reaction, the life time of the catalyst may be extended accordingly (to be greater than 2000 hours). In addition, in the catalyst of the present disclosure, because an alkaline hydrogenation environment is provided by the alkaline earth metal in the carrier, and the alkaline earth metal and Al are uniformly distributed to reduce the strong acid points on the surface of the catalyst, the catalyst selectivity may be increased (to be greater than 98%) and the cracking and dehydroxylated byproducts may also be reduced (to 1% or less). Furthermore, the pyrolysis byproduct is reduced, and a coking rate thereof may also be reduced. Also, the present disclosure is directed to solutions for full hydrogenation and manufacturing process of the catalyst, so as to provide the hydrogenation catalyst with preferable activity, selectivity and stability. Said catalyst can be used together with fixed-bed reactor systems for continuous production of the hydrogenated bisphenol A or derivatives thereof. After the solvent is removed, the product which satisfies the product specifications may then be obtained. Accordingly, processing operation may be simplified, and yield rate and economic benefit of the product may also be improved.

Although the present disclosure has been described with reference to the above embodiments, it is apparent to one of the ordinary skill in the art that modifications to the described embodiments may be made without departing from the spirit of the present disclosure. Accordingly, the scope of the present disclosure will be defined by the attached claims not by the above detailed descriptions.

The invention claimed is:

1. A catalyst, comprising:
   a carrier, represented by a formula: $M_xAl_{(1-x)}O_{(3-x)/2}$, wherein M is an alkaline earth metal, and x is between 0.09 and 0.24; and
   a metal, loaded on the carrier.

2. The catalyst according to claim 1, wherein the alkaline earth metal comprises Mg or Ca.

3. The catalyst according to claim 2, wherein the metal comprises Pd metal.

4. The catalyst according to claim 3, wherein the Pd metal is contained in an amount of between 0.5 wt % and 3 wt % based on the carrier.

5. The catalyst according to claim 1, wherein the metal comprises Pd metal.

6. The catalyst according to claim 5, wherein the Pd metal is contained in an amount of between 0.5 wt % and 3 wt % based on the carrier.

7. The catalyst according to claim 1, wherein the carrier is in amorphous phase.

8. A method for manufacturing a catalyst, comprising:
   preparing a carrier represented by a formula: $M_xAl_{(1-x)}O_{(3-x)/2}$, wherein M is an alkaline earth metal, and x is between 0.09 and 0.24; and
   loading a metal on the carrier.

9. The method for manufacturing the catalyst according to claim 8, wherein the step of preparing the carrier comprises:
   preparing a first solution comprising an alkaline earth metal salt, an aluminum salt, an alkaline and a solvent;
   preparing a second solution comprising the first solution and aluminum oxide; and
   coprecipitating, filtering, water washing and baking the second solution to form the carrier.

10. The method for manufacturing the catalyst according to claim 9, wherein the step of loading the metal on the carrier comprises:
    loading a precursor containing the metal on a surface of the carrier to form a catalyst precursor; and
    coprecipitating, filtering, baking and calcining the catalyst precursor in order to form the catalyst.

11. The method for manufacturing the catalyst according to claim 8, wherein the alkaline earth metal comprises Mg or Ca.

12. The method for manufacturing the catalyst according to claim 11, wherein the metal comprises Pd metal.

13. The method for manufacturing the catalyst according to claim 12, wherein the Pd metal is contained in an amount of between 0.5 wt % and 3 wt % based on the carrier.

14. The method for manufacturing the catalyst according to claim 8, wherein the carrier is in amorphous phase.

15. The method for manufacturing the catalyst according to claim 11, wherein the alkaline earth metal salt comprises an alkaline earth metal nitrate, an alkaline earth metal sulfate, an alkaline earth metal carbonate, or an alkaline earth metal chloride; and the aluminum salt comprises an aluminum nitrate, an aluminum sulfate, an aluminum carbonate, an aluminum oxide, an aluminum hydroxide, or an aluminum chloride.

16. The method for manufacturing the catalyst according to claim 8, wherein the metal comprises Pd metal.

17. The method for manufacturing the catalyst according to claim 16, wherein the Pd metal is contained in an amount of between 0.5 wt % and 3 wt % based on the carrier.

* * * * *